US012599556B2

(12) United States Patent
Bodmeier et al.

(10) Patent No.: US 12,599,556 B2
(45) Date of Patent: Apr. 14, 2026

(54) OPHTHALMIC COMPOSITIONS

(71) Applicant: BIOTHERAVISION, INC.

(72) Inventors: Roland Bodmeier, Berlin (DE); Chin-Ming Chang, Zhubei City (TW)

(73) Assignee: BIOTHERAVISION INC., Chicago, IL (US)

( * ) Notice: Subject to any disclaimer, the term of this patent is extended or adjusted under 35 U.S.C. 154(b) by 341 days.

(21) Appl. No.: 18/264,938

(22) PCT Filed: Feb. 10, 2022

(86) PCT No.: PCT/US2022/015884
§ 371 (c)(1),
(2) Date: Aug. 10, 2023

(87) PCT Pub. No.: WO2022/173878
PCT Pub. Date: Aug. 18, 2022

(65) Prior Publication Data

US 2024/0325305 A1 Oct. 3, 2024

(30) Foreign Application Priority Data

Feb. 11, 2021 (WO) ................ PCT/US2021/017519

(51) Int. Cl.

| | |
|---|---|
| ***A61K 9/10*** | (2006.01) |
| ***A61K 9/00*** | (2006.01) |
| ***A61K 31/407*** | (2006.01) |
| ***A61K 31/56*** | (2006.01) |
| ***A61K 47/10*** | (2017.01) |
| ***A61K 47/18*** | (2017.01) |
| ***A61K 47/32*** | (2006.01) |
| ***A61K 47/38*** | (2006.01) |
| ***A61K 47/40*** | (2006.01) |

(52) U.S. Cl.
CPC .............. *A61K 9/10* (2013.01); *A61K 9/0048* (2013.01); *A61K 31/407* (2013.01); *A61K 31/56* (2013.01); *A61K 47/10* (2013.01); *A61K 47/183* (2013.01); *A61K 47/186* (2013.01); *A61K 47/32* (2013.01); *A61K 47/38* (2013.01); *A61K 47/40* (2013.01)

(58) Field of Classification Search
None
See application file for complete search history.

(56) References Cited

U.S. PATENT DOCUMENTS

2013/0217657 A1* 8/2013 Lindstrom ........... A61K 31/722
514/171

FOREIGN PATENT DOCUMENTS

JP 2020535217 A 12/2020
WO 2019043169 A1 3/2019

OTHER PUBLICATIONS

Written Opinion of International Application No. PCT/US2021/017519, Nov. 11, 2021, 14 pages.
Written Opinion of International Application No. PCT/US2022/015884, Jun. 15, 2022, 16 pages.
Anonymous , "Ophthalmic Glaucoma Agents Advances in Research and Application", Scholarly Editions, 2013, p. 38, paragraph 1.
Loyd, Allen , et al., "Section VII. Sterile Dosage Forms and Delivery Systems, 17 Special Solutions and Suspensions", Ansel's Pharmaceutical Dosage Forms and Drug Delivery Systems, Dec. 23, 2013, p. 616, left-hand column, paragraph 2.
Office Action issued in Japan application No. 2023-547604, Oct. 1, 2025, 19 pages.

* cited by examiner

*Primary Examiner* — Melissa S Mercier
(74) *Attorney, Agent, or Firm* — Synergy IP Group AG; Lily Ackerman

(57) ABSTRACT

The invention provides an aqueous liquid composition for ophthalmic administration, comprising therapeutically effective amounts of a ketorolac compound and of a corticosteroid, wherein the ketorolac compound is present in an essentially dissolved form; wherein the corticosteroid is present in the form of suspended particles; and wherein the composition exhibits an acidic pH of about 6.5 or less. The invention further provides compositions as disclosed herein for use in the prevention or treatment of ocular inflammation and methods for preventing or treating ocular inflammation in a subject.

22 Claims, No Drawings

OPHTHALMIC COMPOSITIONS

CROSS REFERENCE TO RELATED APPLICATIONS

This application is a United States National Stage Application filed under 35 U.S.C. § 371 claiming the benefit of International Application No. PCT/US2022/015884, filed on Feb. 10, 2022, which claims priority to and the benefit of International Application No. PCT/US2021/017519, filed on Feb. 11, 2021, all of which are hereby incorporated herein by reference in their entireties.

DESCRIPTION

Background of the Invention

Ophthalmic compositions comprising the nonsteroidal anti-inflammatory drug (NSAID) ketorolac tromethamine are marketed to treat eye irritation caused by allergies and inflammation occurring after cataract surgery. Similarly, ophthalmic compositions comprising corticosteroid drugs are marketed to treat certain eye conditions due to inflammation, injury, or surgery. Some patients use both drugs to treat irritation or inflammation symptoms. Combining both types of active ingredients into one stable composition to be administered would be more convenient for patients resulting in increased patient compliance. However, combining both types of active ingredients in a single composition is known to be challenging. Chemical incompatibility, stability, safety, and/or efficacy are often negatively affected, and the outcome is unpredictable.

US2013/0217657A1 discloses compositions for topical ophthalmic application, which include an aqueous mixture of steroidal and non-steroidal anti-inflammatory agents in a flowable mucoadhesive polymer, for treating inflammation and inflammatory conditions of the eye. The compositions have a viscosity in the range of about 1,000 to about 30,000 centipoise (cps) or millipascal-second (mPa·s) and gel in the eye after contacting the eye's tear fluid and thus remain in place for prolonged periods of time to provide sustained release of the ophthalmic medicament. The disclosure emphasizes viscosities substantially lower than about 1,000 cps or mPa·s impede the ability to gel upon contact with tears and reduce ocular retention. However, highly viscous compositions may cause unwanted visual disturbances, including optical aberrations such as blurring the vision of the patient and may prevent homogeneous suspension and/or resuspension of solids present in the composition, leading to inaccurate dosing. Furthermore, preparations of specific compositions of US2013/0217657A1 revealed formation of insoluble precipitates of ketorolac tromethamine and chitosan that may reduce bioavailability of ketorolac tromethamine and accuracy of ketorolac tromethamine dosing in such highly viscous compositions.

It is thus an object of the present invention to provide compositions comprising a ketorolac compound and a corticosteroid that are chemically and physically storage stable at room temperature. Such compositions have low viscosities and a ketorolac compound present in an essentially dissolved form. Further objects of the invention will be clear on the basis of the following description of the invention, examples, and claims.

SUMMARY OF THE INVENTION

In a first aspect, the invention relates to an aqueous liquid composition for ophthalmic administration, comprising therapeutically effective amounts of a ketorolac compound and of a corticosteroid, wherein the ketorolac compound is present in an essentially dissolved form; wherein the corticosteroid is present in the form of suspended particles; and wherein the composition exhibits an acidic pH of about 6.5 or less.

In a further aspect, the present invention provides compositions as disclosed herein for use in the prevention or treatment of ocular inflammation.

In yet a further aspect, the invention provides for methods for preventing or treating ocular inflammation in a subject, the methods comprising topically administering any of the compositions disclosed herein to an eye of said subject.

DETAILED DESCRIPTION OF THE INVENTION

The objects are solved by the subject-matter of the independent claims. Advantageous embodiments are described in the dependent claims and subsequent description.

Definitions

Introductorily, some definitions of terms are given which are used throughout the description and claims. The definitions should be used to determine the meaning of the respective expressions unless the context requires a different meaning.

The terms 'a' or 'an' do not exclude a plurality, i.e., the singular forms 'a', 'an' and 'the' should be understood as to include plural referents unless the context clearly indicates or requires otherwise. In other words, all references to singular characteristics or limitations of the present disclosure shall include the corresponding plural characteristic or limitation, and vice versa, unless explicitly specified otherwise or clearly implied to the contrary by the context in which the reference is made. The terms 'a', 'an' and 'the' hence have the same meaning as 'at least one' or as 'one or more' unless defined otherwise. For example, reference to 'an ingredient' includes mixtures of ingredients, and the like.

The terms 'about' or 'ca.' will compensate for variability allowed for in the pharmaceutical industry and inherent in pharmaceutical products, such as differences in content due to manufacturing variation and/or time-induced product degradation. The term allows for any variation, which in the practice of pharmaceuticals would allow the product being evaluated to be considered bioequivalent in a subject to the recited strength of a claimed product.

The terms 'active agent', 'therapeutic agent', 'active pharmaceutical ingredient (API)', 'active principle', 'drug', 'bioactive agent', are used synonymously and refer to a compound or combination of compounds which are pharmaceutically active against an undesired condition.

The term 'composition' refers to any type of composition in which the specified ingredients may be incorporated, optionally along with any further constituents.

The term 'compound' refers to a chemical substance, which is a material consisting of molecules having essentially the same chemical structure and properties. For a small molecular compound, the molecules are typically identical with respect to their atomic composition and structural configuration. For a macromolecular or polymeric compound, the molecules of a compound are highly similar but not all of them are necessarily identical.

The terms 'comprise', 'comprises' and 'comprising' and similar expressions are to be construed in an open and inclusive sense, as 'including, but not limited to'.

The term 'corticosteroid' refers to a steroid hormone that is produced in the adrenal cortex of vertebrates and synthetic analogues of these steroid hormones. The term also includes any salt, ester, acetonide or other hydrolysable prodrug of the corticosteroid. Corticosteroids include drugs that lower inflammation or reduce immune system activity.

The terms 'essentially', 'about', 'approximately', 'substantially' and the like in connection with an attribute or value include the exact attribute or the precise value, as well as any attribute or value typically considered to fall within a normal range or variability accepted in the technical field concerned. For example, 'essentially free of water' means that no water is deliberately included in a composition but does not exclude the presence of residual moisture.

The term 'essentially consisting of' refers to compositions or dosage forms where no further components are added other than those listed. Nevertheless, very small amounts of other materials may potentially be present, such as material inherent impurities. Furthermore, when referring to e.g., 'essentially consisting of A, B, C and optionally D.' this means that no further components are added to a composition or dosage form other than A, B, C and D, with D being an optional component (i.e., not mandatory) in said composition or dosage form.

The term 'essentially free' refers to a composition that contains less than a functional amount of the respective ingredient, typically less than 1% by weight, preferably less than 0.1% or even 0.01%, and including zero percent by weight of the respective ingredient.

The terms 'hydroxypropyl cellulose' and 'HPC' refer to a cellulose ether where some of the hydroxyl groups in the glucose units are substituted with hydroxypropyl groups.

The terms 'hydroxypropyl methylcellulose' and 'HPMC' refer to a cellulose ether where some of the hydroxyl groups in the glucose units are substituted with methyl groups and some others with hydroxypropyl groups.

The term 'ketorolac compound' refers to a compound with the chemical name 5-benzoyl-2,3-dihydro-1H-pyrrolizine-1-carboxylic acid and Chemical Abstracts Service (CAS) number [74103-06-3]. The term 'ketorolac compound' also includes any salt, solvate, ester or other hydrolysable prodrug thereof. Ketorolac has a molecular weight of 255.27 g/mol and the following structure:

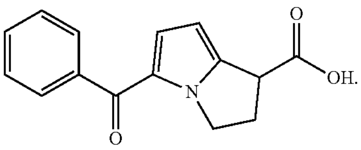 [SMILES: O=C(c1ccccc1)c1ccc2n1CCC2C(=O)O]

The term 'ketorolac tromethamine' refers to a ketorolac compound with the chemical name 2-amino-2-(hydroxymethyl)propane-1,3-diol; 5-benzoyl-2,3-dihydro-1H-pyrrolizine-1-carboxylic acid and CAS number [74103-07-4]. The term 'ketorolac tromethamine' also includes any salt, solvate, ester or other hydrolysable prodrug thereof. Ketorolac tromethamine has a molecular weight of 376.4 g/mol and the following structure:

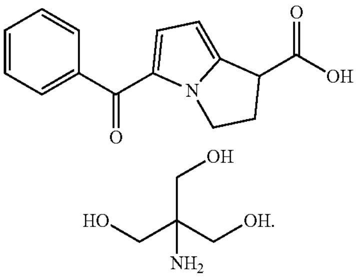

The term 'loteprednol compound' refers to a compound with the chemical name chloromethyl (8S,9S,10R,11S,13S,14S,17R)-11,17-dihydroxy-10,13-dimethyl-3-oxo-7,8,9,11,12,14,15,16-octahydro-6H-cyclopenta[a]phenanthrene-17-carboxylate and CAS number [129260-79-3]. The term 'loteprednol compound' also includes any salt, solvate, ester or other hydrolysable prodrug thereof. Loteprednol has a molecular weight of 394.9 g/mol and the following structure:

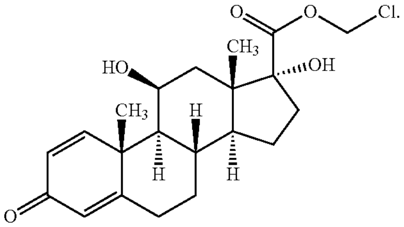

The term 'loteprednol etabonate' refers to a loteprednol compound with the chemical name chloromethyl (8S,9S,10R,11S,13S,14S,17R)-17-ethoxycarbonyloxy-11-hydroxy-10,13-dimethyl-3-oxo-7,8,9,11,12,14,15,16-octahydro-6H-cyclopenta[a]phenanthrene-17-carboxylate and CAS number [82034-46-6]. The term 'loteprednol etabonate' also includes any salt, solvate, ester or other hydrolysable prodrug thereof. Loteprednol etabonate has a molecular weight of 466.9 g/mol and the following structure:

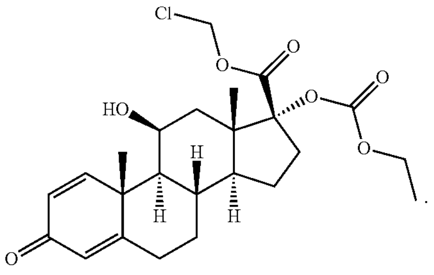

The term 'low-molecular weight polyol' refers to an organic compound containing more than one hydroxyl (—OH) group and having a molecular weight from about 45 g/mol to about 450 g/mol.

The terms, 'one embodiment', 'an embodiment', 'a specific embodiment' and the like mean that a particular feature, property or characteristic, or a particular group or combination of features, properties or characteristics, as referred to in combination with the respective expression, is present in at least one of the embodiments of the invention. The occurrence of these expressions in various places throughout this description do not necessarily refer to the same embodiment. Moreover, the particular features, properties or characteristics may be combined in any suitable manner in one or more embodiments.

The term 'pharmaceutically acceptable' refers to a compound or mixture useful in preparing a pharmaceutical composition that is generally safe, non-toxic and neither biologically nor otherwise undesirable and includes a compound or mixture which is acceptable for human pharmaceutical use.

The term 'poloxamer' refers to nonionic triblock copolymers having a central hydrophobic chain of poly(propylene oxide) flanked by two hydrophilic chains of poly(ethylene oxide). A poloxamer has the general structure:

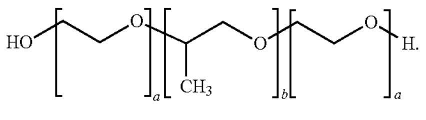

The term 'polymeric viscosity-enhancing agent' refers to polymers that increase or decrease the viscosity of a liquid composition.

The terms 'polyvinylpyrrolidone' and 'povidone' refer to the homopolymer of vinylpyrrolidone. It is also referred to as PVP, polyvidone, and 1-ethenyl-2-pyrrolidon homopolymer.

The term 'preservative' refers to compounds or reagents used to prevent bacterial contamination and/or growth in pharmaceutical compositions.

The term 'prevention' refers to the prevention of a disease, condition or symptom, as well as the prevention of further growth and spread of a reoccurrence or progression after an initial improvement or after initial removal of the cause of the disease, condition or symptom.

The term 'prodrug' refers to a derivative of an active ingredient which converts in the body to the active ingredient. For example, compounds which contain hydroxy or carboxy substituents may form physiologically hydrolysable and acceptable esters as prodrug compounds.

The term 'room temperature' refers to a temperature ranging from 15° C. to 25° C., as is for instance defined by the European Pharmacopoeia or by the WHO guidance 'Guidelines for the Storage of Essential Medicines and Other Health Commodities' (2003).

The term 'subject' typically refers to humans. However, the invention is not limited to humans only and may be employed in animals if required.

The term 'surfactant' refers to amphiphilic compounds or reagents that help solubilize a therapeutically active agent or other insoluble components of the compositions or to stabilize suspensions described herein.

The term 'therapeutically effective amount' refers to that amount which, when administered to a subject for treating or preventing a disease, is sufficient to effect such treatment or prevention for the disease.

The term 'treatment' refers to a therapeutic intervention capable of effecting a cure of a disease, condition or symptom; but also, an improvement, amelioration, control, control of progression, prevention of progression, prevention of reoccurrence, and the like.

The term 'tyloxapol' refers to a nonionic surfactant that is the copolymer of 4-(1,1,3,3-tetramethylbutyl)phenol, formaldehyde and oxirane having the CAS number [25301-02-4] and a monomer molecular weight of 280.4 g/mol.

The particle size distribution was determined by laser diffraction and the reported $D_{10}$, $D_{50}$ and $D_{90}$ values are based on a volume distribution. The $D_{10}$, $D_{50}$ or $D_{90}$ values indicate that 10, 50 or 90%, respectively, of the particle volume is contained in particles that are smaller than these values.

Compositions

The invention provides aqueous liquid compositions for ophthalmic administration which are homogenous suspensions upon shaking and before administration. The compositions have viscosities suitable for ocular comfort and exhibit physical and chemical stability while stored. Polymers may increase the viscosity of eye drops and enhance adhesion to the mucus layer of tears. In practice, the optimal viscosity of an eye drop is often a compromise between comfort and vision requirements. Increased viscosity increases retention time but causes unwanted visual disturbances, including optical aberrations.

In a first aspect, the invention provides aqueous liquid compositions for ophthalmic administration, comprising therapeutically effective amounts of a ketorolac compound and of a corticosteroid, wherein the ketorolac compound is present in an essentially dissolved form; wherein the corticosteroid is present in the form of suspended particles; and wherein the composition exhibits an acidic pH of about 6.5 or less. In some embodiments, the aqueous liquid compositions for ophthalmic administration comprise therapeutically effective amounts of a ketorolac compound and of a corticosteroid, wherein the ketorolac compound is present in an essentially dissolved form; wherein the corticosteroid is present in the form of suspended particles; wherein the composition exhibits an acidic pH of about 6.5 or less; and wherein the viscosity of the aqueous liquid composition is in the range from about 1 to about 60 centipoise (cps) or millipascal-second (mPa·s). Compositions with such low viscosities allow for homogeneous suspension of the suspended particles of the corticosteroid and less unwanted visual disturbances, including optical aberrations such as blurring of vision. In some embodiments, the ketorolac compound is ketorolac tromethamine. In some embodiments, the corticosteroid is a compound selected from dexamethasone, prednisolone, fluorometholone, betamethasone, difluprednate, triamcinolone, remexolone, loteprednol, and clobetasol. In some particular embodiments, the corticosteroid is a loteprednol compound. In other particular embodiments, the loteprednol compound is loteprednol etabonate. In other particular embodiments, the ketorolac compound is ketorolac tromethamine and the corticosteroid is loteprednol etabonate. In other particular embodiments, the compositions comprise any salt, solvate, ester, acetonide, or other hydrolysable prodrug, where applicable, of any compound present in the composition. The pharmaceutically acceptable analogues of such salts, solvates, esters, acetonides, or other prodrugs are also contemplated.

In some embodiments, the concentration of ketorolac tromethamine in the composition is from about 0.2 wt. % to about 1.0 wt. %, and preferably from about 0.3 wt. % to about 0.6 wt. %. In other embodiments, the concentration of ketorolac tromethamine is about 0.45 wt. %, 0.5 wt. % or about 1.0 wt. %. In some embodiments, the concentration of loteprednol etabonate in the composition is from about 0.1 wt. % to about 1.2 wt. %, about 0.3 wt. % to about 1.2 wt. %, and about 0.5 wt. % or about 1.0 wt. %. In other embodiments, the concentration of loteprednol etabonate in the composition is preferably about 0.5 wt. % or about 1.0 wt. %.

As used herein, compositions may be prepared in either wt. % or w/v %, and the units may be used interchangeably unless otherwise specifically specified, e.g., in the Tables disclosed herein. For example, when a range is expressed as "from about 0.2 wt. % to about 1.0 wt. %", the range may also be expressed as "from about 0.2 w/v % to about 1.0 w/v %". However, for the Tables where point references are used, the units are specifically specified in the first line of the table, e.g., Tables 1-3 include values in wt. % and Tables 4 and 7-8 include values in w/v %.

In some embodiments, the composition exhibits an acidic pH of about 6.5 or less. In other embodiments, the composition exhibits a pH of about 6.0 or less. In other embodiments, the composition exhibits a pH of about 5.5 or less. In yet other embodiments, the composition exhibits a pH of about 5-6. In other particular embodiments, the composition exhibits a pH of about 5.5. Prior known, stable compositions comprising ketorolac compounds are typically formulated at higher pH such as about 7.0 to about 7.4. However, loteprednol compounds are typically unstable at higher pH levels greater than 6.5. Despite this apparent pH incompatibility, the inventors have unexpectedly found that it is possible to formulate compositions comprising a ketorolac compound and a loteprednol compound at lower pH values of about 6.5 or less.

In some embodiments, the composition is essentially free of a buffer system. Buffer systems are well known in the art and are solutions that resist a change in pH when acid or base is added to it. Generally, buffer solutions contain a mixture of a weak acid and its conjugate base or a weak base and its conjugate acid. Common buffer systems used in ophthalmic compositions include citrate, phosphate, Tris-HCl (Tris), and borate buffers.

In other embodiments, the composition is essentially free of sodium chloride.

In yet other embodiments, the composition is essentially free of poloxamer.

In yet other embodiments, the composition is essentially free of a cross-linked, carboxy containing polymer. Such polymers include polycarbophil. Inclusion of cross-linked, carboxy containing polymers produces highly viscous gel compositions which would impede homogeneous suspension of solid particles and potentially result in inaccurate dosing. Furthermore, viscous gels may cause unwanted visual disturbances, including optical aberrations such as blurring of vision.

In yet other embodiments, the composition is essentially free of chitosan. Compositions containing both chitosan and ketorolac form insoluble precipitates due to the positively charged chitosan forming an insoluble salt complex with the negatively charged ketorolac compound as shown in Examples 5 and 6 disclosed herein. Inclusion of chitosan in the compositions disclosed herein may reduce bioavailability of the ketorolac compound and accuracy of the ketorolac compound dosing due to formation of the insoluble precipitates.

In some embodiments, the composition is further characterized in that it exhibits a surface tension in the range from about 20 to 70 dyne per centimeter (dyn/cm) or about 0.020 to 0.070 newton per meter (N/m), zeta potential in the range from about +/−10 to +/−40 millivolt (mV), and/or a viscosity in the range from about 1 to 60 centipoise (cps) or millipascal-second (mPa·s). In other embodiments, the composition is further characterized in that it exhibits a surface tension in the range from about 20 to 70 dyne per centimeter (dyn/cm) or about 0.020 to 0.070 newton per meter (N/m), and/or zeta potential in the range from about +/−10 to +/−40 millivolt (mV). In yet other embodiments, the composition is further characterized in that it exhibits a viscosity in the range from about 1 to about 60 centipoise (cps) or millipascal-second (mPa·s). As used herein, viscosity refers to viscosity as measured by a Brookfield viscometer. Generally, the test solution is stored at room temperature for about 2 h prior to testing. The test solution is placed on the measurement chamber using a pipette, and a proper speed is selected for the spindle according to the expected viscosity of the sample. The Brookfield Viscometer determines viscosity by measuring the force to turn the spindle in the solution at a given rate.

In some embodiments, the composition further comprises:

(a) a polymeric viscosity-enhancing agent;

(b) a non-ionic surfactant; and/or (c) a low-molecular weight polyol.

In some embodiments, the polymeric viscosity-enhancing agent is a non-ionic, water-soluble polymer, and preferably selected from hydroxypropyl cellulose (HPC), hydroxypropyl methylcellulose (HPMC), and polyvinylpyrrolidone (PVP). In some particular embodiments, the polymeric viscosity-enhancing agent is polyvinylpyrrolidone. In other particular embodiments, the weight ratio of the ketorolac tromethamine to the polyvinylpyrrolidone is from about 1:10 to about 10:1, about 1:10 to about 5:1, and about 1:3 to about 2:1. In other particular embodiments, the weight ratio of the ketorolac tromethamine to the polyvinylpyrrolidone is from about 1:10 to about 5:1, and preferably from about 1:3 to about 2:1. In other embodiments the weight ratio of the ketorolac tromethamine to the polyvinylpyrrolidone is from about 1:1 to about 1:2.

In some embodiments, the non-ionic surfactant is tyloxapol; and wherein the concentration of tyloxapol in the composition is from about 0.1 wt. % to about 1.2 wt. %, and preferably from greater than about 0.2 wt. % to less than about 1.0 wt. %.

In some embodiments, the low-molecular weight polyol is glycerol; and wherein the concentration of glycerol in the composition is from about 0.5 wt. % to about 2.5 wt. %. In other embodiments, the concentration of glycerol in the composition is from about 1.0 wt. % to about 2.0 wt. %.

In some embodiments, the composition comprises a further polymeric viscosity-enhancing agent, said further polymeric viscosity-enhancing agent being selected from anionic carbohydrates, preferably hyaluronic acid, gellan gum, or carboxymethyl cellulose, including any salts thereof. In some particular embodiments, the anionic carbohydrate is at least partially neutralised carboxymethyl cellulose. In other particular embodiments, the carboxymethyl cellulose is sodium carboxymethyl cellulose (NaCMC), and the weight ratio of the sodium carboxymethyl cellulose to the polyvinylpyrrolidone is from about 1:10 to about 10:1, about 1:10 to about 5:1, and about 1:2 to about 2:1. In other particular embodiments, the weight ratio of the sodium carboxymethyl cellulose to the polyvinylpyrrolidone is from about 1:10 to about 5:1, and preferably from about 1:2 to about 2:1.

In some embodiments, the composition further comprises a cyclodextrin, preferably 2-hydroxypropyl-β-cyclodextrin or sulfobutylether-β-cyclodextrin; and wherein the molar ratio of the cyclodextrin to the ketorolac tromethamine is from about 1:85 to about 6:1, and preferably from about 1:25 to about 1:2. In some particular embodiments, the cyclodextrin is 2-hydroxypropyl-β-cyclodextrin. In other particular embodiments, the cyclodextrin is sulfobutylether-β-cyclodextrin.

In some embodiments, the composition further comprises ethylenediaminetetraacetic acid (EDTA), preferably at a concentration of about 0.1 wt. % or lower. In some particular embodiments, the EDTA is sodium ethylenediaminetetraacetic acid (NaEDTA).

In other embodiments, the composition further comprises a preservative. Preservatives used in ophthalmic preparations are known in the art, including, for example, benzalkonium chloride (BAK), chlorobutanol, sodium perborate, and stabilized oxychloro complex. In some particular embodiments, the preservative is benzalkonium chloride (BAK).

In some embodiments, the carboxymethyl cellulose is sodium carboxymethyl cellulose, and wherein the composition consists essentially of:

(a) ketorolac tromethamine, preferably about 0.3 wt. % to about 0.6 wt. %;
(b) a corticosteroid;
(c) tyloxapol, preferably about 0.2 wt. % to about 1 wt. %;
(d) polyvinylpyrrolidone, preferably about 0.4 wt. % to about 0.8 wt. %;
(e) sodium carboxymethyl cellulose, preferably about 0.4 wt. % to about 0.8 wt. %;
(f) glycerol, preferably about 0.5 wt. % to about 2.5 wt. %;
(g) EDTA, preferably about 0.01 wt. % to about 0.1 wt. %;
(h) benzalkonium chloride, preferably about 0.005 wt. % to about 0.02 wt. %;
(i) water; and optionally
(k) 2-hydroxypropyl-β-cyclodextrin, preferably about 0.1 wt. % to about 0.8 wt. %, and/or an acid or base to adjust the pH, wherein the pH of the composition is about 5-6.

In some embodiments of the compositions described herein, the suspended particles of the corticosteroid have a $D_{90}$ of about less than 20 μm, of about less than 10 μm, or of about less than 5 μm. In other embodiments of the compositions described herein, the suspended particles of the corticosteroid have a $D_{90}$ of about less than 3 μm, of about less than 1 μm, or of about less than 0.5 μm. In yet other embodiments of the compositions described herein, the suspended particles have a $D_{50}$ of about less than 1 μm. In some embodiments, the compositions described herein comprise particles in the submicron particle size range. In other embodiments, the compositions described herein comprise particles in the nanometer particle size range. Generally, smaller particle sizes promote better bioavailability of the corticosteroid.

Uses and Methods

In a second aspect, the invention provides uses and methods of preventing or treating ocular conditions with the compositions disclosed herein.

In some embodiments, the invention provides a composition for use in the prevention or treatment of ocular inflammation. In other embodiments, the ocular inflammation is associated with, or occurring subsequent to, cataract surgery. In other embodiments, the ocular inflammation is associated with seasonal allergic conjunctivitis. In some embodiments, the use involves ophthalmic administration of the composition once a day, twice daily, or three times daily.

In some embodiments, the invention provides a method for preventing or treating ocular inflammation in a subject, said method comprising topically administering any of the compositions disclosed herein to an eye of said subject. In some embodiments, the ocular inflammation is associated with, or occurring subsequent to, cataract surgery. In other embodiments, the ocular inflammation is associated with seasonal allergic conjunctivitis. In yet other embodiments, the administering of the composition occurs once a day, twice daily, or three times daily.

The following examples serve to illustrate the invention, however, should not be understood as restricting the scope of the invention.

EXAMPLES

Materials and Methods

The following materials were used to prepare exemplary ophthalmic compositions described herein: ketorolac tromethamine, loteprednol etabonate, tyloxapol, poloxamer, carbomer, polyvinylpyrrolidone (povidone), ethylenediaminetetraacetic acid (EDTA), sodium ethylenediaminetetraacetic acid (NaEDTA), glycerol, benzalkonium chloride (BAK), sodium carboxymethyl cellulose (NaCMC), 2-hydroxypropyl-β-cyclodextrin, sulfobutylether-β-cyclodextrin, hydrochloric acid, sodium hydroxide, and purified water.

Viscosity is measured using a Brookfield viscometer. The test solution is stored at room temperature for about 2 h prior to testing. The test solution is placed on the measurement chamber using a pipette, and a proper speed is selected for the spindle according to the expected viscosity of the sample. The Brookfield Viscometer determines viscosity by measuring the force to turn the spindle in the solution at a given rate.

Example 1: Screening Experiments

Compositions shown in Table 1 and Table 2 were prepared with various surfactants and viscosity agents to evaluate the physicochemical stability of loteprednol etabonate and ketorolac combination suspensions over time. Tyloxapol, poloxamer, and mixtures of thereof were evaluated as surfactants. Polyvinylpyrrolidone, sodium carboxymethylcellulose, carbomer, and mixtures thereof were evaluated as viscosity agents.

TABLE 1

Screening Experiments, Compositions F2-F5

| Ingredient, wt. % | F2.1 | F2.2 | F3.1 | F3.2 | F4.1 | F4.2 | F5.1 | F5.2 |
|---|---|---|---|---|---|---|---|---|
| Ketorolac tromethamine | 0.5 | | 0.5 | | 0.5 | | 0.5 | |
| Loteprednol etabonate | 0.5 | | 0.5 | | 0.5 | | 0.5 | |

TABLE 1-continued

| Screening Experiments, Compositions F2-F5 | | | | | | | | |
|---|---|---|---|---|---|---|---|---|
| Ingredient, wt. % | F2.1 | F2.2 | F3.1 | F3.2 | F4.1 | F4.2 | F5.1 | F5.2 |
| Tyloxapol | 0.1 | | 0.1 | | 0.3 | | 0.3 | |
| Poloxamer (Pluronic F127) | 0.6 | | 0.6 | | 0.6 | | 0.6 | |
| Povidone (Kollidon 30) | | | | | | | | |
| Sodium CMC (7HF PH) | | | 0.5 | | | | 0.5 | |
| Carbomer (Carbopol 974P) | 1 | | | | 1 | | | |
| Glycerin | 1.6 | | 1.6 | | 1.6 | | 1.6 | |
| EDTA | 0.05 | | 0.05 | | 0.05 | | 0.05 | |
| BAK | 0.005 | | 0.005 | | 0.005 | | 0.005 | |
| pH | 5.0 | 5.5 | 5.0 | 5.5 | 5.0 | 5.5 | 5.0 | 5.5 |
| Water | q.s. | | | | | | | |
| | % Assay Loteprednol at 25° C. | | | | | | | |
| Time 0 | 116.5 | 107.3 | 105.6 | 102.3 | 104.0 | 99.8 | 102.5 | 96.6 |
| Time 8 months | n/a | 102.2 | 96.1 | 91.7 | 99.8 | 94.8 | 89.9 | 85.3 |
| Time 19 months | n/a | n/a | n/a | n/a | n/a | n/a | n/a | n/a |
| | % Assay Ketorolac at 25° C. | | | | | | | |
| Time 0 | 109.8 | 102.9 | 104.6 | 103.5 | 101.6 | 97.6 | 102.8 | 98.0 |
| Time 8 months | n/a | 105.9 | 97.6 | 94.0 | 100.1 | 104.1 | 91.0 | 87.7 |
| Time 19 months | n/a | n/a | n/a | n/a | n/a | n/a | n/a | n/a |
| | Particle size (μm, D90) at 25° C. | | | | | | | |
| Time 0 | 1.14 | 0.88 | 0.70 | 1.39 | 0.46 | 0.41 | 0.35 | 0.60 |
| Time 8 months | 1.93 | 1.30 | 1.65 | 2.59 | n/a | n/a | 0.39 | 1.24 |
| | Physical Appearance at 25° C. G: Gel; S: Suspension sediments | | | | | | | |
| Time 0 | G | G | S | S | G | G | S | S |
| Time 3 months | G | G | S | S | G | G | S | S |

TABLE 2

| Screening Experiments, Compositions F7-F10 | | | | | | | | |
|---|---|---|---|---|---|---|---|---|
| Ingredient, wt. % | F7.1 | F7.2 | F8.1 | F8.2 | F9.1 | F9.2 | F10.1 | F10.2 |
| Ketorolac tromethamine | 0.5 | | 0.5 | | 0.5 | | 0.5 | |
| Loteprednol etabonate | 0.5 | | 0.5 | | 0.5 | | 0.5 | |
| Tyloxapol | 0.1 | | 0.1 | | 0.3 | | 0.3 | |
| Poloxamer (Pluronic F127) | | | | | | | | |
| Povidone (Kollidon 30) | 0.6 | | 0.6 | | 0.6 | | 0.6 | |
| Sodium CMC (7HF PH) | | | 0.5 | | | | 0.5 | |
| Carbomer (Carbopol 974P) | 1 | | | | 1 | | | |
| Glycerin | 1.6 | | 1.6 | | 1.6 | | 1.6 | |
| EDTA | 0.05 | | 0.05 | | 0.05 | | 0.05 | |
| BAK | 0.005 | | 0.005 | | 0.005 | | 0.005 | |
| pH | 5.0 | 5.5 | 5.0 | 5.5 | 5.0 | 5.5 | 5.0 | 5.5 |
| Water | q.s. | | | | | | | |
| | % Assay Loteprednol at 25° C. | | | | | | | |
| Time 0 | 101.8 | 102.7 | 106.1 | 101.6 | 95.5 | 102.4 | 100.5 | 100.5 |
| Time 8 months | 99.1 | 100.2 | 99.7 | 94.9 | 99.8 | 99.8 | 96.9 | 99.1 |
| Time 19 months | 104.1 | 100.8 | 93.7 | 100.2 | 99.2 | 101.7 | 100.8 | 100.3 |
| | % Assay Ketorolac at 25° C. | | | | | | | |
| Time 0 | 99.2 | 101.9 | 105.6 | 103.7 | 96.0 | 101.7 | 102.5 | 103.4 |
| Time 8 months | 102.2 | 102.6 | 100.8 | 97.9 | 99.3 | 104.9 | 100.1 | 99.4 |
| Time 19 months | 88.8 | 96.3 | 65.9 | 81.6 | 89.4 | 90.8 | 95.8 | 97.8 |

TABLE 2-continued

| Screening Experiments, Compositions F7-F10 | | | | | | | | |
|---|---|---|---|---|---|---|---|---|
| Ingredient, wt. % | F7.1 | F7.2 | F8.1 | F8.2 | F9.1 | F9.2 | F10.1 | F10.2 |
| | Particle size (μm, D90) at 25° C. | | | | | | | |
| Time 0 | 0.41 | 0.41 | 0.35 | 0.42 | 0.40 | 0.40 | 0.33 | 0.41 |
| Time 8 months | n/a | n/a | 0.47 | 0.52 | n/a | n/a | 0.37 | 0.48 |
| | Physical Appearance at 25° C. G: Gel; S: Suspension sediments | | | | | | | |
| Time 0 | G | G | S | S | G | G | S | S |
| Time 3 months | G | G | S | S | G | G | S | S |

The carbomer containing formulations (F2, F4, F7, and F9) formed high viscous gels which cannot be resuspended to produce a homogeneous composition. Therefore, carbomer-containing compositions were not further pursued.

Compositions F2 and F3 comprising a mixture of tyloxapol at 0.1 wt. % and poloxamer at 0.6 wt. % were physically unstable as evidenced from an increase in the particle size over time. Therefore, these compositions were not selected for further evaluation.

Composition F5 comprising a mixture of tyloxapol at 0.3 wt. % and poloxamer at 0.6 wt. % as surfactant and sodium carboxymethyl cellulose (NaCMC or sodium CMC) as the viscosity agent showed significant decrease of loteprednol and ketorolac assay values over time. Therefore, these compositions were not selected for further evaluation.

Compositions F8 and F10 comprising tyloxapol without the presence of poloxamer, and mixture of povidone and NaCMC as viscosity agent achieved desired physical and chemical stability, re-suspendability, and low viscosity. These compositions were further evaluated for optimization.

Example 2: Preparation of Exemplary Compositions

Based on the screening experiments of Example 1, compositions comprising a loteprednol compound, a ketorolac compound, tyloxapol, povidone, sodium carboxymethyl cellulose, and additional components were further optimized and evaluated.

A milling aid solution was prepared by dissolving povidone, tyloxapol, glycerol, and EDTA in purified water and filtering the solution using a 0.2 μm filter. Loteprednol etabonate powder was then dispersed into the milling aid solution using high shear mixing with an ULTRA-TURRAX. The loteprednol etabonate dispersion was transferred into a milling chamber (Dyno-Mill) which was then filled with beads (zirconium oxide beads). The suspension slurry was milled for a specific duration and discharged from the chamber. To ensure complete transfer from the milling chamber, the suspension slurry was diluted with a washing medium during transfer.

The mixture of the milled suspension slurry, beads, and washing medium was collected and filtered using a dialysis membrane and vacuum pump. Additional washing medium was used for washing milling beads during the filtration process. The suspension slurry is typically irradiation sterilized before further mixing with the rest of the formulation ingredients. For micron size formulations, a milling step may not be necessary.

Ketorolac tromethamine was dissolved in the milling aid solution to prepare a ketorolac tromethamine stock solution. Sodium carboxymethyl cellulose was dissolved in the milling aid solution to prepare a sodium carboxymethyl cellulose stock solution. Benzalkonium chloride may be added in the ketorolac tromethamine stock solution. The sodium carboxymethyl cellulose stock solution and ketorolac tromethamine stock solution were filtered through 0.2 μm filter and then mixed with the loteprednol etabonate suspension slurry until homogeneous. The pH was adjusted with 0.1 M HCl/0.1 M NaOH.

Specific exemplary compositions prepared as described above in Example 2 are summarized below in Table 3.

Example 3: Preparation of Exemplary Compositions with Cyclodextrin

Exemplary compositions further comprising cyclodextrin were prepared as in Example 2 above, with the addition of cyclodextrin as an additional component in the milling aid composition. Alternatively, cyclodextrin was added as a powder to the loteprednol etabonate suspension slurry after milling.

Specific exemplary compositions prepared as described above in Example 3 are summarized below in Table 4.

TABLE 3

| Formulation Compositions for Panel I Stability Study | | | | | |
|---|---|---|---|---|---|
| | Formulation | | | | |
| Ingredient, wt. % | 10 A | 10 B | 10 C | 10 D | 10 E |
| ketorolac tromethamine* | | | 0.5 | | |
| loteprednol etabonate | 1.0 | 1.0 | 0.5 | 0.5 | 0.5 |
| Tyloxapol | | | 0.3 | | |
| Povidone K 30 | | | 0.6 | | |
| Glycerin | | | 1.60 | | |
| Na CMC 7 HF | | | 0.50 | | |
| EDTA | | | 0.05 | | |
| Benzalkonium chloride | | | 0.005 | | |
| 1M NaOH/HCl | 5.5 | 6.0 | 5.5 | 6.0 | 5.0 |
| water | | | q.s. | | |

*Free acid equivalent

TABLE 4

| Formulation Compositions for Panel II Stability Study | | | | | | |
|---|---|---|---|---|---|---|
| | Formulation | | | | | |
| | Microsuspension No sterilization | | | Nanosuspension γ-irradiated, intermediate | | |
| Ingredient, w/v % | F1 | F2 | F3 | F7 | F8 | F9 |
| ketorolac tromethamine* | | | 0.5 | | | |
| loteprednol etabonate | | | 0.5 | | | |
| Tyloxapol | | | 0.3 | | | |
| Povidone K 30 | | | 0.6 | | | |
| Glycerin | | | 1.60 | | | |
| Na CMC 7 HF | | | 0.50 | | | |
| EDTA | | | 0.05 | | | |
| Benzalkonium chloride | | | 0.01 | | | |
| 2-Hydroxypropyl-β-cyclodextrin | 0 | 0.15 | 0.6 | 0 | 0.15 | 0.6 |
| 1M NaOH/HCl | 5.5 | 5.5 | 5.5 | 5.5 | 5.5 | 5.5 |
| water | | | q.s. | | | |

*Free acid equivalent

Example 4: Stability Studies of Exemplary Compositions

The stability of the exemplary compositions was investigated using gradient high performance liquid chromatography analysis at different storage time points of 1 month, 3 months, 6 months, 9 months, and 11 months. The amount of each active ingredient and related degradation substances, pH, osmolality, particle size distribution, and viscosity were measured for each composition at each time point.

Ketorolac tromethamine (KT) exhibited stability in all compositions. The degradation of loteprednol etabonate (LE) showed a pH dependency, thus pH was optimized for loteprednol etabonate stability.

The results of the Panel I stability studies for the compositions shown in Table 3 are summarized in Table 5. The suspension slurry was not irradiation sterilized in the preparation of Panel 1 formulations.

In Tables 5 and 6, below, the term "RS" refers to "related substance"; "LOQ" refers to "Limit of Quantification; "RRT" refers to "relative retention time"; and LR refers to "loteprednol etabonate related".

TABLE 5

| Panel I Formulation Stability Data at 25° C. for 11 months | | | | | | |
|---|---|---|---|---|---|---|
| | | $t_0$ | 25° C./60% RH Time, months | | | |
| Parameter | | 0 | 3 | 6 | 9 | 11 |
| | | Panel I, 10 A | | | | |
| Assay, % | Loteprednol etabonate | 95.37 | 95.30 | 93.91 | 90.12 | 91.98 |
| | Ketorolac tromethamine | 101.06 | 100.76 | 99.56 | 98.10 | 97.23 |
| RS, % (LOQ 0.05%) | Total LE impurity | <LOQ | 1.15 | 1.79 | 2.54 | 3.74 |
| | Individual LE impurity ≥0.1% | <LOQ | RRT 0.46: 1.15 | RRT 0.46: 1.79 | RRT 0.46: 2.54 | LR 1: 1.09<br>LR 2: 2.54<br>LR 3: 0.11 |
| | Total KT impurity | <LOQ | <LOQ | <LOQ | 3.08 | <LOQ |
| | Individual KT impurity ≥0.1% | <LOQ | <LOQ | <LOQ | RRT 0.83: 3.08 | <LOQ |
| pH | | 5.31 | 5.38 | 5.34 | 5.12 | 5.14 |
| Osmolality, mOsmol/kg | | 297 | 295 | 297 | 300 | 299 |
| Viscosity, mPa · s or cps | | 2.74 | 4.8 | 3.1 | 4.8 | 4.3 |
| Particle size, μm | $D_{10}$ | 0.07 | 0.07 | 0.08 | 0.06 | 0.07 |
| | $D_{50}$ | 0.12 | 0.12 | 0.12 | 0.13 | 0.14 |
| | $D_{90}$ | 0.21 | 0.20 | 0.18 | 0.26 | 0.37 |
| Physical appearance | | White, sediment | Clear, sediment | Clear, sediment | Clear, sediment | Clear, sediment |
| Re-dispersibility, inversion times | | <10 | <10 | <20 | <10 | <10 |
| | | Panel I, 10 B | | | | |
| Assay, % | Loteprednol etabonate | 103.36 | 99.14 | 99.37 | 97.41 | 95.62 |
| | Ketorolac tromethamine | 105.58 | 102.93 | 97.20 | 96.76 | 101.82 |
| RS, % (LOQ 0.05%) | Total LE impurity | <LOQ | 1.22 | 2.00 | 2.97 | 3.88 |
| | Individual LE impurity ≥0.1% | <LOQ | RRT 0.46: 1.22 | RRT 0.46: 2.00 | RRT 0.46: 2.97 | LR 1: 0.82<br>LR 2: 2.94<br>LR 3: 0.11 |
| | Total KT impurity | <LOQ | <LOQ | <LOQ | 2.32 | <LOQ |
| | Individual KT impurity ≥0.1% | <LOQ | <LOQ | <LOQ | RRT 0.83: 2.32 | <LOQ |
| pH | | 5.75 | 5.77 | 5.67 | 5.54 | 5.4 |
| Osmolality, mOsmol/kg | | 298 | 297 | 303 | 300 | 298 |
| Viscosity, mPa · s or cps | | 1.8 | 2.6 | 5.1 | 4.3 | 2.5 |

TABLE 5-continued

| Panel I Formulation Stability Data at 25° C. for 11 months | | | | | | |
|---|---|---|---|---|---|---|
| | | $t_0$ | 25° C./60% RH Time, months | | | |
| Parameter | | 0 | 3 | 6 | 9 | 11 |
| Particle size, μm | $D_{10}$ | 0.06 | 0.07 | 0.07 | 0.07 | 0.06 |
| | $D_{50}$ | 0.12 | 0.12 | 0.13 | 0.12 | 0.12 |
| | $D_{90}$ | 0.21 | 0.22 | 0.25 | 0.22 | 0.25 |
| Physical appearance | | White, sediment | Clear, sediment | Clear, sediment | Clear, sediment | Clear, sediment |
| Re-dispersibility, inversion times | | <10 | <10 | <20 | <10 | <10 |
| | | Panel I, 10 C | | | | |
| Assay, % | Loteprednol etabonate | 103.83 | 99.44 | 99.13 | 96.32 | 95.97 |
| | Ketorolac tromethamine | 105.64 | 101.25 | 101.39 | 98.80 | 101.82 |
| RS, % (LOQ 0.05%) | Total LE impurity | <LOQ | 1.15 | 1.96 | 2.89 | 3.85 |
| | Individual LE impurity ≥0.1% | <LOQ | RRT 0.46: 1.15 | RRT 0.46: 1.96 | RRT 0.46: 2.89 | LR 1: 0.76 LR 2: 3.08 |
| | Total KT impurity | <LOQ | <LOQ | <LOQ | 1.05 | <LOQ |
| | Individual KT impurity ≥0.1% | <LOQ | <LOQ | <LOQ | RRT 0.83: 1.05 | <LOQ |
| pH | | 5.44 | 5.53 | 5.51 | 5.37 | 5.39 |
| Osmolality, mOsmol/kg | | 277 | 272 | 271 | 273 | 275 |
| Viscosity, mPa · s or cps | | 2.4 | 2.4 | 2.9 | 5.0 | 5.7 |
| Particle size, μm | $D_{10}$ | 0.7 | 0.7 | 0.08 | 0.07 | 0.07 |
| | $D_{50}$ | 0.12 | 0.12 | 0.12 | 0.12 | 0.13 |
| | $D_{90}$ | 0.22 | 0.22 | 0.17 | 0.21 | 0.24 |
| Physical appearance | | White, sediment | Clear, sediment | Clear, sediment | Clear, sediment | Clear, sediment |
| Re-dispersibility, inversion times | | <10 | <10 | <20 | <10 | <10 |
| | | Panel I, 10 D | | | | |
| Assay, % | Loteprednol etabonate | 101.68 | 98.75 | 100.95 | 97.99 | 98.97 |
| | Ketorolac tromethamine | 103.26 | 101.98 | 102.96 | 100.39 | 100.08 |
| RS, % (LOQ 0.05%) | Total LE impurity | <LOQ | 1.21 | 2.12 | 3.30 | 4.01 |
| | Individual LE impurity ≥0.1% | <LOQ | RRT 0.46: 1.21 | RRT 0.46: 2.12 | RRT 0.46: 3.30 | LR 1: 0.54 LR 2: 3.47 |
| | Total KT impurity | <LOQ | <LOQ | <LOQ | 0.75 | <LOQ |
| | Individual KT impurity ≥0.1% | <LOQ | <LOQ | <LOQ | RRT 0.83: 0.75 | <LOQ |
| pH | | 5.87 | 5.90 | 5.86 | 5.79 | 6.63 |
| Osmolality, mOsmol/kg | | 282 | 273 | 269 | 273 | 275 |
| Viscosity, mPa · s or cps | | 2.1 | 1.1 | 1.9 | 4.4 | 3.3 |
| Particle size, μm | $D_{10}$ | 0.06 | 0.07 | 0.06 | 0.07 | 0.07 |
| | $D_{50}$ | 0.12 | 0.12 | 0.12 | 0.12 | 0.12 |
| | $D_{90}$ | 0.24 | 0.20 | 0.21 | 0.20 | 0.22 |
| Physical appearance | | White, sediment | Clear, sediment | Clear, sediment | Clear, sediment | Turbid, sediment |
| Re-dispersibility, inversion times | | <10 | <10 | <20 | <20 | <10 |
| | | Panel I, 10 E | | | | |
| Assay, % | Loteprednol etabonate | 98.13 | 97.45 | 97.34 | 96.15 | 96.32 |
| | Ketorolac tromethamine | 98.29 | 99.32 | 98.39 | 97.50 | 98.20 |
| RS, % (LOQ 0.05%) | Total LE impurity | <LOQ | 1.03 | 1.61 | 2.27 | 3.51 |
| | Individual LE impurity ≥0.1% | <LOQ | RRT 0.46: 1.03 | RRT 0.46: 1.61 | RRT 0.46: 2.27 | LR 1: 1.14 LR 2: 2.27 LR 5: 0.11 |
| | Total KT impurity | <LOQ | <LOQ | <LOQ | 1.59 | <LOQ |
| | Individual KT impurity ≥0.1% | <LOQ | <LOQ | <LOQ | RRT 0.83: 1.59 | <LOQ |
| pH | | 4.99 | 5.04 | 5.07 | 4.99 | 5.02 |
| Osmolality, mOsmol/kg | | 269 | 264 | 267 | 265 | 267 |
| Viscosity, mPa · s or cps | | 2.9 | 3.1 | 3.8 | 3.1 | 5.6 |

TABLE 5-continued

Panel I Formulation Stability Data at 25° C. for 11 months

| Parameter | | $t_0$ 0 | 25° C./60% RH Time, months 3 | 6 | 9 | 11 |
|---|---|---|---|---|---|---|
| Particle size, μm | $D_{10}$ | 0.08 | 0.06 | 0.07 | 0.07 | 0.07 |
| | $D_{50}$ | 0.12 | 0.12 | 0.13 | 0.12 | 0.12 |
| | $D_{90}$ | 0.19 | 0.21 | 0.22 | 0.20 | 0.22 |
| Physical appearance | | White, sediment | Clear, sediment | Clear, sediment | Clear, sediment | Clear, sediment |
| Re-dispersibility, inversion times | | <10 | <10 | <20 | <10 | <10 |

Degradation of loteprednol occurred in the formulation as expected within an acceptable level. Minimal degradation of ketorolac was achieved in this formulation and all other test parameters such as pH, osmolality, viscosity and particle size also remained stable throughout the stability study.

The results of the Panel II stability studies at the accelerated condition (40° C.) for the compositions shown in Table 4 are summarized in Table 6. The suspension slurry of Panel 2 formulations F7, F8, and F9 were irradiation sterilized.

TABLE 6

Panel II Formulation Stability Data at 40° C. for 1 month

| Parameter | | $t_0$ 0 | 40° C./25% RH Time, months 1 |
|---|---|---|---|
| | | Panel II, F1 | |
| Assay, % | Loteprednol etabonate | 100.10 | 99.76 |
| | Ketorolac tromethamine | 98.59 | 99.63 |
| RS, % (LOQ 0.05%) | Total LE impurity | <LOQ | 1.35 |
| | Individual LE impurity ≥0.1% | <LOQ | LR 1: 0.16<br>LR 2: 1.19 |
| | Total KT impurity | <LOQ | <LOQ |
| | Individual KT impurity ≥0.1% | <LOQ | <LOQ |
| pH | | 5.5 | 5.5 |
| Osmolality, mOsmol/kg | | 275 | 274 |
| Viscosity, mPa · s or cps | | 2.9 | 2.2 |
| Surface Tension, mN/m | | 38.04 | 38.01 |
| Zeta potential, mV | | −30.8 | −23.4 |
| Particle size, μm | $D_{10}$ | 2.21 | 2.07 |
| | $D_{50}$ | 4.56 | 4.56 |
| | $D_{90}$ | 9.14 | 9.99 |
| Physical appearance | | Homogeneous, White | White sediment |
| Re-dispersibility, inversion times | | n.a. | 15-20 |
| | | Panel II, F2 | |
| Assay, % | Loteprednol etabonate | 100.99 | 99.58 |
| | Ketorolac tromethamine | 98.50 | 99.05 |
| RS, % (LOQ 0.05%) | Total LE impurity | <LOQ | 1.41 |
| | Individual LE impurity ≥0.1% | <LOQ | LR 1: 0.15<br>LR 2: 1.26 |
| | Total KT impurity | <LOQ | <LOQ |
| | Individual KT impurity ≥0.1% | <LOQ | <LOQ |
| pH | | 5.5 | 5.5 |
| Osmolality, mOsmol/kg | | 276 | 276 |
| Viscosity, mPa · s or cps | | 2.1 | 1.7 |
| Surface Tension, mN/m | | 38.23 | 37.67 |
| Zeta potential, mV | | −25.5 | −19.1 |

TABLE 6-continued

Panel II Formulation Stability Data at 40° C. for 1 month

| Parameter | | $t_0$ 0 | 40° C./25% RH Time, months 1 |
|---|---|---|---|
| Particle size, μm | $D_{10}$ | 1.99 | 2.19 |
| | $D_{50}$ | 4.47 | 4.93 |
| | $D_{90}$ | 10.27 | 11.70 |
| Physical appearance | | Homogeneous, White | White sediment |
| Re-dispersibility, inversion times | | n.a. | 15-20 |
| | | Panel II, F3 | |
| Assay, % | Loteprednol etabonate | 100.74 | 99.61 |
| | Ketorolac tromethamine | 98.11 | 98.70 |
| RS, % (LOQ 0.05%) | Total LE impurity | <LOQ | 2.24 |
| | Individual LE impurity ≥0.1% | <LOQ | LR 1: 0.13<br>LR 2: 2.11 |
| | Total KT impurity | <LOQ | <LOQ |
| | Individual KT impurity ≥0.1% | <LOQ | <LOQ |
| pH | | 5.5 | 5.4 |
| Osmolality, mOsmol/kg | | 283 | 284 |
| Viscosity, mPa · s or cps | | 2.9 | 2.5 |
| Surface Tension, mN/m | | 38.04 | 38.28 |
| Zeta potential, mV | | −3.4 | −25.3 |
| Particle size, μm | $D_{10}$ | 2.24 | 2.10 |
| | $D_{50}$ | 4.92 | 4.62 |
| | $D_{90}$ | 10.35 | 9.90 |
| Physical appearance | | Homogeneous, White | White sediment |
| Re-dispersibility, inversion times | | n.a. | 15-20 |
| | | Panel II, F7 | |
| Assay, % | Loteprednol etabonate | 98.28 | 97.77 |
| | Ketorolac tromethamine | 98.82 | 98.33 |
| RS, % (LOQ 0.05%) | Total LE impurity | 0.93 | 2.61 |
| | Individual LE impurity ≥0.1% | LR 1: 0.13<br>LR 2: 0.49<br>LR 3: 0.32 | LR 1: 0.32<br>LR 2: 2.02<br>LR 3: 0.26 |
| | Total KT impurity | <LOQ | <LOQ |
| | Individual KT impurity ≥0.1% | <LOQ | <LOQ |
| pH | | 5.5 | 5.5 |
| Osmolality, mOsmol/kg | | 284 | 292 |
| Viscosity, mPa · s or cps | | 4.1 | 4.2 |
| Surface Tension, mN/m | | 38.18 | 38.07 |
| Zeta potential, mV | | −26.7 | −25.3 |
| Particle size, μm | $D_{10}$ | 0.07 | 0.07 |
| | $D_{50}$ | 0.16 | 0.17 |
| | $D_{90}$ | 1.66 | 2.00 |
| Physical appearance | | White | White sediment |
| Re-dispersibility, inversion times | | 5-10 | 5-10 |

TABLE 6-continued

Panel II Formulation Stability Data at 40° C. for 1 month

| | Parameter | $t_0$ 0 | 40° C./ 25% RH Time, months 1 |
|---|---|---|---|
| | | Panel II, F8 | |
| Assay, % | Loteprednol etabonate | 98.65 | 97.86 |
| | Ketorolac tromethamine | 99.36 | 99.20 |
| RS, % | Total LE impurity | 0.97 | 2.34 |
| (LOQ 0.05%) | Individual LE impurity ≥0.1% | LR 1: 0.15<br>LR 2: 0.49<br>LR 3: 0.33 | LR 1: 0.34<br>LR 2: 1.74<br>LR 3: 0.26 |
| | Total KT impurity | <LOQ | <LOQ |
| | Individual KT impurity ≥0.1% | <LOQ | <LOQ |
| pH | | 5.5 | 5.5 |
| Osmolality, mOsmol/kg | | 294 | 294 |
| Viscosity, mPa · s or cps | | 4.4 | 1.3 |
| Surface Tension, mN/m | | 37.95 | 37.59 |
| Zeta potential, mV | | −24.7 | −19.8 |
| Particle size, μm | $D_{10}$ | 0.07 | 0.07 |
| | $D_{50}$ | 0.16 | 0.16 |
| | $D_{90}$ | 1.05 | 1.67 |
| Physical appearance | | White | White sediment |
| Re-dispersibility, inversion times | | 5-10 | 5-10 |
| | | Panel II, F9 | |
| Assay, % | Loteprednol etabonate | 99.00 | 98.91 |
| | Ketorolac tromethamine | 98.81 | 99.08 |
| RS, % | Total LE impurity | 0.94 | 2.21 |
| (LOQ 0.05%) | Individual LE impurity ≥0.1% | LR 1: 0.14<br>LR 2: 0.49<br>LR 3: 0.31 | LR 1: 0.32<br>LR 2: 1.61<br>LR 3: 0.29 |
| | Total KT impurity | <LOQ | <LOQ |
| | Individual KT impurity ≥0.1% | <LOQ | <LOQ |
| pH | | 5.5 | 5.5 |
| Osmolality, mOsmol/kg | | 310 | 309 |
| Viscosity, mPa · s or cps | | 4.2 | 4.8 |
| Surface Tension, mN/m | | 37.42 | 38.39 |
| Zeta potential, mV | | −23.6 | −23.5 |
| Particle size, μm | $D_{10}$ | 0.07 | 0.07 |
| | $D_{50}$ | 0.16 | 0.17 |
| | $D_{90}$ | 1.13 | 2.52 |
| Physical appearance | | White | White sediment |
| Re-dispersibility, inversion times | | 5-10 | 5-10 |

Similar to the results from the Panel 1 study, degradation of loteprednol occurred in the formulation as expected. Minimal degradation of ketorolac was achieved in this formulation and all other test parameters such as pH, osmolality, viscosity, surface tension, zeta potential, and particle size remained stable throughout the stability study.

Example 5: Investigation of Chitosan as Additive

Chitosan was investigated as an additive in an exemplary embodiment of the compositions disclosed herein. The composition of this example included the following components.

TABLE 7

Components of Chitosan Containing Composition

| Ingredients, w/v % | EY-05 BTV300 C19 |
|---|---|
| Ketorolac Tromethamine | 0.4 |
| Tyloxapol | 0.3 |
| Chitosan | 0.025 |
| PVP K30 | 0.6 |
| NaEDTA | 0.05 |
| Glycerine | 2.0 |

TABLE 7-continued

Components of Chitosan Containing Composition

| Ingredients, w/v % | EY-05 BTV300 C19 |
|---|---|
| 2-hydroxypropyl-β-cyclodextrin | 0.6 |
| NaCMC 7 LF PH | 0.5 |
| Benzalkonium Chloride | 0.012 |
| pH adjusted with Sodium Hydroxide | 5.5 |

Given that chitosan is positively charged, and ketorolac compounds, NaCMC, and NaEDTA are negatively charged in aqueous solutions, it was hypothesized that chitosan may form insoluble precipitates with one or more of these components due to formation of insoluble salt complexes. In this exemplary embodiment, loteprednol etabonate was excluded to assure the visibility of potential precipitates formed during the preparations.

Two distinct approaches were investigated. In a first experiment, a solution of fully dissolved chitosan was added to a clear, colorless solution of NaCMC and NaEDTA, resulting in formation of white flocculant precipitate; and a solution having a pH of 4.1. Chitosan is fully soluble at pH 4, suggesting an incompatibility of chitosan with NaCMC and/or NaEDTA. In a second experiment, a solution of fully dissolved chitosan was added to a clear, colorless solution of glycerine, tyloxapol, PVP, HP-b-cyclodextrin, and ketorolac tromethamine having a pH 5.1. Upon addition of the two solutions, white flocculates formed immediately with a resulting solution of pH 3.8. When the pH 3.8 solution containing the white flocculates is pH adjusted to the final formulation of pH 5.5, the white flocculates persist. If the preparation is repeated excluding ketorolac tromethamine, no precipitates form. Moreover, chitosan is fully soluble at pH 3.8. Therefore, the observed white precipitates are a chitosan/ketorolac tromethamine insoluble complex. Precipitate formation would reduce the bioavailability of ketorolac and accuracy of ketorolac dosing, highlighting the incompatibility of chitosan in such compositions.

Example 6: Comparative Studies with Chitosan Containing Gel Compositions

Chitosan containing compositions of ketorolac tromethamine and loteprednol etabonate were prepared using the methods disclosed in US2013/0217657A1, specifically compositions 7 and 8 of Table 6. The compositions included the following components:

TABLE 8

Components of Comparative Compositions 7 and 8

| Ingredients, w/v % | Composition 7 | Composition 8 |
|---|---|---|
| Ketorolac Tromethamine | 0.4 | 0.2 |
| Loteprednol Etabonate | 0.5 | 0.5 |
| Poloxamer 407 | 0.2 | |
| Chitosan | 0.025 | |
| Polycarbophil | 0.95 | |
| Sodium Edetate | 0.1 | |
| NaCl | 0.35 | |
| Mannitol | 1.0 | |
| Benzalkonium Chloride | 0.003 | |
| HCl 2N | 1.5 | |
| pH adjusted with Sodium Hydroxide | 6.8 | |

Compositions 7 and 8 were prepared by combining polycarbophil, sodium chloride, and sodium edetate in water and stirring for 0.5 hours. The composition was autoclaved at 121° C. for 45 minutes and cooled to room temperature to produce a white opaque suspension. An aqueous solution of chitosan was prepared using hydrochloric acid and added into the polycarbophil suspension to produce a free flowing, white opaque suspension. Mannitol, Poloxamer 407, and ketorolac tromethamine were dissolved in water to form a clear colorless solution, and loteprednol etabonate was added to the solution by dry particle addition to form a white suspension. The mannitol, poloxamer 407, ketorolac tromethamine, and loteprednol etabonate suspension was added to the polycarbophil, sodium chloride, sodium edetate, chitosan suspension and the pH adjusted to 6.8 to form the final formulation. The final formulation was a white, smooth gel with a viscosity of 7921 mPa·s or cps as measured by Brookfield viscometer.

Since loteprednol etabonate was present as a solid dispersion in compositions 7 and 8, it was not possible to visually observe if chitosan and ketorolac tromethamine formed insoluble precipitates as was observed in Example 5, above. In order to investigate the hypothesis, compositions 7 and 8 were prepared as described above, but excluding loteprednol etabonate. In a first experiment, chitosan was added to a clear, colorless solution of mannitol and poloxamer 407. In a second experiment, chitosan was added to a clear, colorless solution of mannitol, poloxamer 407, and ketorolac tromethamine. Upon addition of chitosan to the clear, colorless solution of mannitol and poloxamer 407, a clear colorless solution of pH 3.9 formed. In contrast, when chitosan was added to clear, colorless solutions of mannitol, poloxamer 407, and ketorolac tromethamine, white suspensions of pH 4.7 (composition 7, high ketorolac concentration) and pH 4.6 (composition 8, low ketorolac concentration) formed. The compositions 7 and 8 were then pH adjusted to 6.8 to form the final formulation. Both compositions contain white flocculates deriving from the chitosan/ketorolac salt complex. Therefore, both compositions 7 and 8 do not comprise a ketorolac compound in an essentially dissolved form.

Item List

Amongst others, the following list of numbered items are specific embodiments comprised by the present invention:

1. An aqueous liquid composition for ophthalmic administration, comprising therapeutically effective amounts of a ketorolac compound and of a corticosteroid, wherein the ketorolac compound is present in an essentially dissolved form; wherein the corticosteroid is present in the form of suspended particles; wherein the composition exhibits an acidic pH of about 6.5 or less; and wherein the viscosity of the aqueous liquid composition is in the range from about 1 to about 60 centipoise (cps) or millipascal-second (mPa·s).
2. The composition of item 1, wherein the corticosteroid is selected from dexamethasone, prednisolone, fluorometholone, betamethasone, difluprednate, triamcinolone, remexolone, loteprednol, and clobetasol, or any salt, ester, acetonide or other hydrolysable prodrug thereof.
3. The composition of item 1, wherein the corticosteroid is selected from dexamethasone, prednisolone, fluorometholone, betamethasone, difluprednate, triamcinolone, remexolone, loteprednol, and clobetasol, or any salt, ester, or acetonide thereof.
4. The composition of any one of the preceding items, being essentially free of a buffer system, wherein essentially free refers to the composition comprising less than a functional amount of the buffer system, typically less than 1% by weight, preferably less than 0.1% or even 0.01%, and including zero percent by weight of the buffer system.
5. The composition of any one of the preceding items, being essentially free of sodium chloride, wherein essentially free refers to the composition comprising less than a functional amount of the sodium chloride, typically less than 1% by weight, preferably less than 0.1% or even 0.01%, and including zero percent by weight of the sodium chloride.
6 The composition of any one of the preceding items, having a pH of about 5-6.
7. The composition of any one of the preceding items, further characterised in that it exhibits a surface tension in the range from about 20 to 70 dyne per centimeter (dyn/cm) or about 0.020 to 0.070 newton per meter (N/m), and/or a zeta potential in the range from about +/−10 to +/−40 millivolt (mV).
8. The composition of any one of the preceding items, wherein the ketorolac compound is ketorolac tromethamine.
9. The composition of item 8, wherein the concentration of ketorolac tromethamine in the composition is from about 0.2 wt. % to about 1.0 wt. %, and preferably from about 0.3 wt. % to about 0.6 wt. %.
10. The composition of any one of the preceding items, wherein the corticosteroid is a loteprednol compound, and preferably loteprednol etabonate.
11. The composition of item 10, wherein the concentration of loteprednol etabonate in the composition is from about 0.1 wt. % to about 1.2 wt. %, and preferably about 0.5 wt. % or about 1.0 wt. %.
12. The composition of any one of the preceding items, further comprising:
    (a) a polymeric viscosity-enhancing agent;
    (b) a non-ionic surfactant; and/or
    (c) a low-molecular weight polyol;

wherein the low-molecular weight polyol refers to an organic compound comprising more than one hydroxyl (—OH) group and having a molecular weight from about 45 g/mol to about 450 g/mol.

13. The composition of item 12, wherein the polymeric viscosity-enhancing agent is a non-ionic, water-soluble polymer, and preferably selected from hydroxypropyl cellulose (HPC), hydroxypropyl methylcellulose (HPMC), and polyvinylpyrrolidone (PVP).
14. The composition of any one of items 12 to 13, wherein the polymeric viscosity-enhancing agent is polyvinylpyrrolidone.
15. The composition of any one of items 13 to 14, wherein the weight ratio of the ketorolac tromethamine to the polyvinylpyrrolidone is from about 1:10 to about 5:1, and preferably from about 1:3 to about 2:1.
16. The composition of item 12, wherein the non-ionic surfactant is tyloxapol; and wherein the concentration of tyloxapol in the composition is from about 0.1 wt. % to about 1.2 wt. %, and preferably from greater than about 0.2 wt. % to less than about 1.0 wt. %.
17. The composition of item 12, wherein the low-molecular weight polyol is glycerol; and wherein the concentration of glycerol in the composition is from about 0.5 wt. % to about 2.5 wt. %.
18. The composition of any one of items 12 to 17, comprising a further polymeric viscosity-enhancing agent, said further polymeric viscosity-enhancing agent being selected from anionic carbohydrates, preferably hyaluronic acid, gellan gum, or carboxymethyl cellulose, including any salts thereof.

19. The composition of item 18, wherein the anionic carbohydrate is at least partially neutralised carboxymethyl cellulose.

20. The composition of any one of items 18 to 19, wherein the carboxymethyl cellulose is sodium carboxymethyl cellulose, and wherein the weight ratio of the sodium carboxymethyl cellulose to the polyvinylpyrrolidone is from about 1:10 to about 5:1, and preferably from about 1:2 to about 2:1.

21. The composition of any one of the preceding items, being essentially free of poloxamer, wherein essentially free refers to the composition comprising less than a functional amount of the poloxamer, typically less than 1% by weight, preferably less than 0.1% or even 0.01%, and including zero percent by weight of the poloxamer.

22. The composition of any one of items 8 to 21, further comprising a cyclodextrin, preferably 2-hydroxypropyl-β-cyclodextrin or sulfobutylether-β-cyclodextrin; and wherein the molar ratio of the cyclodextrin to the ketorolac tromethamine is from about 1:85 to about 6:1, and preferably from about 1:25 to about 1:2.

23. The composition of any one of the preceding items, further comprising ethylenediaminetetraacetic acid (EDTA), preferably at a concentration of about 0.1 wt. % or lower.

24. The composition of any one of the preceding items, further comprising a preservative.

25. The composition of any one of items 23 to 24, wherein the carboxymethyl cellulose is sodium carboxymethyl cellulose, and wherein the composition consists essentially of (a) ketorolac tromethamine, preferably about 0.3 wt. % to about 0.6 wt. %;
(b) a corticosteroid;
(c) tyloxapol, preferably about 0.2 wt. % to about 1 wt. %;
(d) polyvinylpyrrolidone, preferably about 0.4 wt. % to about 0.8 wt. %;
(e) sodium carboxymethyl cellulose, preferably about 0.4 wt. % to about 0.8 wt. %;
(f) glycerol, preferably about 0.5 wt. % to about 2.5 wt. %;
(g) EDTA, preferably about 0.01 wt. % to about 0.1 wt. %;
(h) benzalkonium chloride, preferably about 0.005 wt. % to about 0.02 wt. %;
(i) water; and optionally
(k) 2-hydroxypropyl-β-cyclodextrin, preferably about 0.1 wt. % to about 0.8 wt. %, and/or an acid or base to adjust the pH, wherein the pH of the composition is about 5-6.

26. The composition of any one of the preceding items, wherein the suspended particles have a $D_{90}$ of about less than 20 μm.

27. The composition of any one of the preceding items, wherein the suspended particles have a $D_{90}$ of about less than 3 μm.

28. The composition of any one of the preceding items, wherein the suspended particles have a $D_{50}$ of about less than 1 μm.

29. The composition of any one of the preceding items, being essentially free of a cross-linked, carboxy containing polymer, wherein essentially free refers to the composition comprising less than a functional amount of the cross-linked, carboxy containing polymer, typically less than 1% by weight, preferably less than 0.1% or even 0.01%, and including zero percent by weight of the cross-linked, carboxy containing polymer.

30. The composition of any one of the preceding items, being essentially free of chitosan, wherein essentially free refers to the composition comprising less than a functional amount of the chitosan, typically less than 1% by weight, preferably less than 0.1% or even 0.01%, and including zero percent by weight of the chitosan.

31. The composition of any one of the preceding items, for use in the prevention or treatment of ocular inflammation.

32. The composition for use of item 31, wherein the ocular inflammation is associated with, or occurring subsequent to, cataract surgery.

33. The composition for use of item 31, wherein the ocular inflammation is associated with seasonal allergic conjunctivitis.

34. The composition for use of any one of items 31 to 33, wherein the use involves ophthalmic administration of the composition once a day, twice daily, or three times daily.

35. A method for preventing or treating ocular inflammation in a subject, said method comprising topically administering the composition of any one of items 1 to 34 to an eye of said subject.

36. The method of item 35, wherein the subject has undergone cataract surgery.

37. The method of item 35, wherein the ocular inflammation is associated with seasonal allergic conjunctivitis.

38. The method of item 35, wherein the administering occurs once a day, twice daily, or three times daily.

39. The use of the compositions of any one of items 1 to 30 for the manufacture of a medicament for the prevention or treatment of ocular inflammation.

40. The use of item 39, wherein the ocular inflammation is associated with, or occurring subsequent to, cataract surgery.

41. The use of item 39, wherein the ocular inflammation is associated with seasonal allergic conjunctivitis.

42. The use of any one of items 39 to 41, wherein the use involves ophthalmic administration of the composition once a day, twice daily, or three times daily.

The invention claimed is:

1. An aqueous liquid composition for ophthalmic administration, comprising therapeutically effective amounts of a ketorolac compound and of a corticosteroid, wherein the ketorolac compound is present in an essentially dissolved form; wherein the corticosteroid is present in the form of suspended particles; wherein the composition exhibits an acidic pH of about 6.5 or less; and wherein the viscosity of the aqueous liquid composition is in the range from about 1 to about 60 centipoise (cps) or millipascal-second (mPa·s).

2. The composition of claim 1, wherein the corticosteroid is selected from dexamethasone, prednisolone, fluorometholone, betamethasone, difluprednate, triamcinolone, remexolone, loteprednol, and clobetasol, or any salt, ester, acetonide or other hydrolysable prodrug thereof.

3. The composition of claim 1, being essentially free of a buffer system.

4. The composition of claim 1, being essentially free of sodium chloride.

5. The composition of claim 1, having a pH of about 5-6.

6. The composition of claim 1, further characterised in that it exhibits a surface tension in the range from about 20 to 70 dyne per centimeter (dyn/cm) or about 0.020 to 0.070 newton per meter (N/m), and/or a zeta potential in the range from about +/−10 to +/−40 millivolt (mV).

7. The composition of claim 1, wherein the ketorolac compound is ketorolac tromethamine.

8. The composition of claim 1, wherein the corticosteroid is a loteprednol compound.

9. The composition of claim 1, further comprising:

(a) a polymeric viscosity-enhancing agent;

(b) a non-ionic surfactant; and/or (c) a low-molecular weight polyol;

wherein the low-molecular weight polyol refers to an organic compound comprising more than one hydroxyl (—OH) group and having a molecular weight from about 45 g/mol to about 450 g/mol.

10. The composition of claim 9, wherein the polymeric viscosity-enhancing agent is a non-ionic, water-soluble polymer.

11. The composition of claim 10, wherein the polymeric viscosity-enhancing agent is polyvinylpyrrolidone.

12. The composition of claim 9, wherein the non-ionic surfactant is tyloxapol; and wherein the concentration of tyloxapol in the composition is from about 0.1 wt. % to about 1.2 wt. %.

13. The composition of claim 9, wherein the low-molecular weight polyol is glycerol; and wherein the concentration of glycerol in the composition is from about 0.5 wt. % to about 2.5 wt. %.

14. The composition of claim 9, comprising a further polymeric viscosity-enhancing agent, said further polymeric viscosity-enhancing agent being selected from anionic carbohydrates including any salts thereof.

15. The composition of claim 1, being essentially free of poloxamer.

16. The composition of claim 7, further comprising a cyclodextrin.

17. The composition of claim 1, further comprising ethylenediaminetetraacetic acid (EDTA).

18. The composition of claim 17, wherein the composition consists essentially of (a) a ketorolac tromethamine;

(b) a corticosteroid;

(c) a tyloxapol;

(d) a polyvinylpyrrolidone;

(e) a sodium carboxymethyl cellulose;

(f) a glycerol;

(g) EDTA;

(h) a benzalkonium chloride;

(i) a water; and optionally (k) a 2-hydroxypropyl-β-cyclodextrin and/or an acid or base to adjust the pH, wherein the pH of the composition is about 5-6.

19. The composition of claim 1, wherein the suspended particles have a $D_{90}$ of about less than 20 μm.

20. The composition of claim 1, being essentially free of a cross-linked, carboxy containing polymer.

21. The composition of claim 1, being essentially free of chitosan.

22. A method for preventing or treating ocular inflammation in a subject, said method comprising topically administering the composition of claim 1 to an eye of said subject.

* * * * *